United States Patent [19]

Kita et al.

[11] Patent Number: 5,711,036
[45] Date of Patent: Jan. 27, 1998

[54] GOGGLES HAVING VERTICAL BAND INSERTION HOLES

[75] Inventors: Tadashi Kita; Tomoyuki Yashiro, both of Higashi-Osaka, Japan

[73] Assignee: Yamamoto Kogaku Co., Ltd., Higashi-Osaka, Japan

[21] Appl. No.: 762,959

[22] Filed: Dec. 10, 1996

[51] Int. Cl.⁶ .................................................. A61F 9/02
[52] U.S. Cl. .......................................... 2/452; 2/426
[58] Field of Search ............................. 2/426, 431, 436, 2/438, 442, 448, 450, 452; 351/140, 142, 149, 150, 153

[56] References Cited

U.S. PATENT DOCUMENTS

| | | | |
|---|---|---|---|
| 2,126,379 | 8/1938 | Fischer | 2/452 |
| 4,264,987 | 5/1981 | Runckel. | |
| 5,046,199 | 9/1991 | Hall | 2/446 |
| 5,341,516 | 8/1994 | Keim | 2/452 |
| 5,390,373 | 2/1995 | Flory | 2/445 |
| 5,502,844 | 4/1996 | Alvarado | 2/428 |

FOREIGN PATENT DOCUMENTS 53-153700  12/1978  Japan.
1-23494    7/1989  Japan.

*Primary Examiner*—C. D. Crowder
*Assistant Examiner*—Larry D. Worrell, Jr.
*Attorney, Agent, or Firm*—Oblon, Spivak, McClelland, Maier & Neustadt, P.C.

[57] ABSTRACT

Goggles enabling fine adjustments of eyecups and providing an increased degree of fitting freedom onto wearer's face are provided including a pair of right and left eyecups, a nasal belt interconnecting respective opposing inner end portions of the eyecups, and an elastic band connecting to respective outer end portions of the eyecups, each of the outer end portions of the eyecups defining a band insertion hole vertically extending therethrough.

6 Claims, 7 Drawing Sheets

PRIOR ART

GOGGLES HAVING VERTICAL BAND INSERTION HOLES

BACKGROUND OF THE INVENTION

The present invention relates to goggles for protecting eyes in various activities such as swimming, skiing, motorcycling and different operations.

FIGS. 14 to 16 illustrate an example of conventional goggles of this type (refer to, for example, Japanese Unexamined Utility Model Publication Nos. SHO 53-153700 and HEI 1-23494.

Goggles 21 shown are for use in swimming and include a pair of right and left eyecups 22,22, a nasal belt 23 interconnecting opposing inner ends, or nasal ends, of the eyecups 22,22, an elastic band 24 connecting to outer ends of the eyecups 22,22, and an annular cushion pad 25 having a soft elasticity and bonded to the rear peripheral edge of each eyecup 22.

On each of the opposing inner ends of the eyecups 22,22 is provided a nasal belt mounting seat 26 protruding therefrom. The nasal belt mounting seat 26 defines a substantially rectangular belt insertion hole 27 extending through the seat 26 in the thicknesswise direction thereof. The nasal belt 23 is molded of a flexible material such as rubber or a resin into a rectangular shape in section as having a plurality of engagement projections 28 on the side adapted to face opposite the face of the wearer or on the reverse side. The nasal belt 23 is inserted into the belt insertion hole 27, so that any of the engagement projections 28 engages the peripheral edge of the belt insertion hole 27 on the wearer's face side.

Each eyecup 22 defines at an outer end portion thereof an elastic band insertion hole 29 horizontally extending therethrough. The elastic band 24 is a single continuous strap of rubber and is inserted through the band insertion holes 29,29 and the both ends 24A,24A thereof are connected together by being inserted through an adjustment buckle 30 in a superposed fashion. Thus, the goggles 21 are double-supported at the back of the wearer's head by the elastic band 24, resulting in improved wearing stability.

With the foregoing conventional goggles, fine fitting adjustment is difficult and requires time due to the elastic band which is relatively heavy. Further, since the elastic band is inserted through the eyecups horizontally, or in the direction toward and away from the wearer's face, the eyecups are likely to be twisted by the elastic band. Consequently, the goggles suffer poor fit onto the wear's face and, hence, the eyecups are easy to come out of position due to impact occurring when the wearer plunges into water in swimming, permitting undesirable introduction of water into the eyecups.

The present invention has been attained in view of the foregoing problems, and therefore, it is an object of the invention to provide goggles which enable easy fine adjustment of eyecups and enjoy increased degree of fitting freedom.

SUMMARY OF THE INVENTION

According to one aspect of the present invention, there is provided goggles comprising a pair of right and left eyecups, a nasal belt interconnecting respective opposing inner end portions of the eyecups, and an elastic band connecting to respective outer end portions of the eyecups, each of the outer end portions of the eyecups defining a band insertion hole vertically extending therethrough.

With this feature of the present invention, the elastic band inserted through the band insertion holes of the eyecups is easy to move vertically relative to the eyecups thereby facilitating fine positional adjustments of the eyecups relative to the wearer's face. Moreover, since the elastic band inserted through the band insertion holes pulls the upper and lower end portions of each band insertion hole evenly rearward, the eyecups are unlikely to be twisted forward and backward, thus resulting in improved positional stability and an increased degree of fitting freedom. Accordingly, the goggles can be stably fitted onto the wearer's face without cushion pads.

According to another aspect of the present invention, the band insertion hole is formed into an elongate circular configuration having a longitudinal end portion with a smaller radius of curvature on the side closer to a lens portion of each eyecup than the radius of curvature of an opposite longitudinal end portion on the side closer to the outer end portion of the eyecup.

With this feature, if the elastic band is formed to have a substantially circular cross sectional configuration, the eyecups are each pivotable relative to the elastic band so as to be movable more flexibly. This results in the goggles having improved fit onto the wearer's face. In addition, the elastic band can be inserted through the band insertion holes with ease.

According to yet another aspect of the present invention, the elastic band comprises portions having a substantially circular cross sectional configuration and portions having a substantially rectangular cross sectional configuration.

With this feature, the elastic band has a lightened weight, and further, even if the elastic band is twisted, the twisting stress can be absorbed by the portions having a substantially circular cross sectional configuration, thus enabling fine adjustments of the eyecups and providing improved wearing stability.

According to yet another aspect of the present invention, the portions having a substantially circular cross sectional configuration of the elastic band have a radius equal to or slightly smaller than the larger radius of curvature of the band insertion hole, while the portions having a substantially rectangular cross sectional configuration of the elastic band have a width equal to or slightly smaller than a longitudinal size of the band insertion hole.

With this feature, it is possible to insert the elastic band through the band insertion holes of the eyecups very easily.

According to still another aspect of the present invention, the portions having a substantially circular cross sectional configuration are adapted to be located as extending through the band insertion holes, while the portions having a substantially rectangular cross sectional configuration are adapted to be located on the back of wearer's head.

With this feature, each eyecup is pivotable about the corresponding portion having a substantially circular cross sectional configuration of the elastic band thereby providing improved fit properties. If this feature is applied to swimming goggles, such swimming goggles will be subjected to a decreased resistance of water in swimming. Furthermore, the goggles are double-supported at the back of the wearer's head by the portions having a substantially rectangular cross sectional configuration of the elastic band, resulting in improved wearing stability.

According to a further aspect of the present invention, the eyecups each have a peripheral wall having a rear edge face adapted to come into direct contact with wearer's face.

Goggles with such feature have a lightened weight and hence are best suited for competitive swimming. Further, since conventionally required cushion pads are unnecessary, the goggles can be manufactured with a decreased cost. In addition, the goggles offer an increased degree of fitting freedom and hence can be stably fitted onto the wearer's face without cushion pads.

The foregoing and other object, features and attendant advantages of the present invention will be readily appreciated as the same becomes better understood by reference to the following detailed description when considered in connection with the accompanying drawings.

DESCRIPTION OF THE PREFERRED EMBODIMENTS

The present invention will now be described in detail with reference to the drawings.

Figure 1:
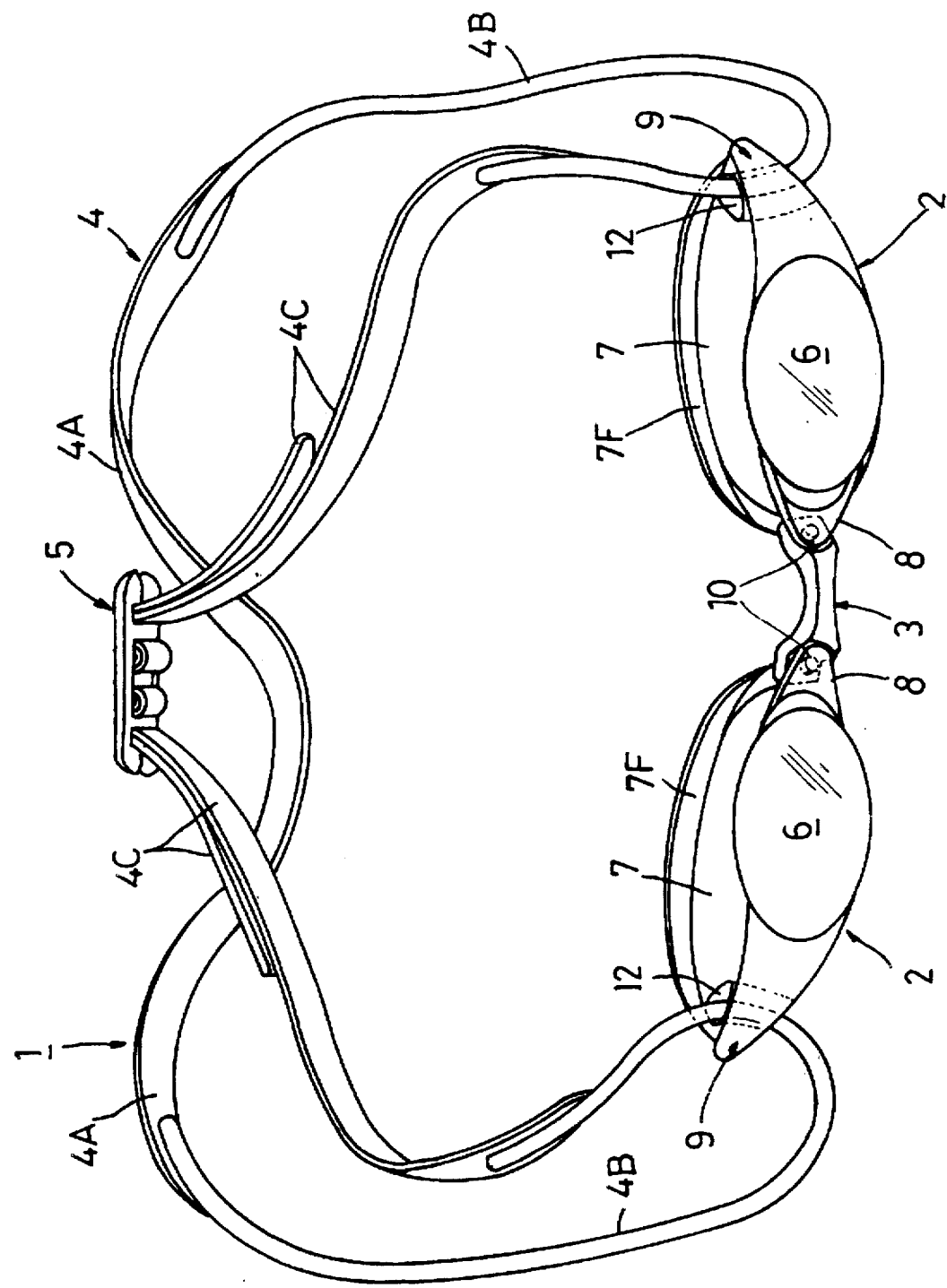
FIG. 1 is a perspective view showing one embodiment of the present invention.
Figure 2:
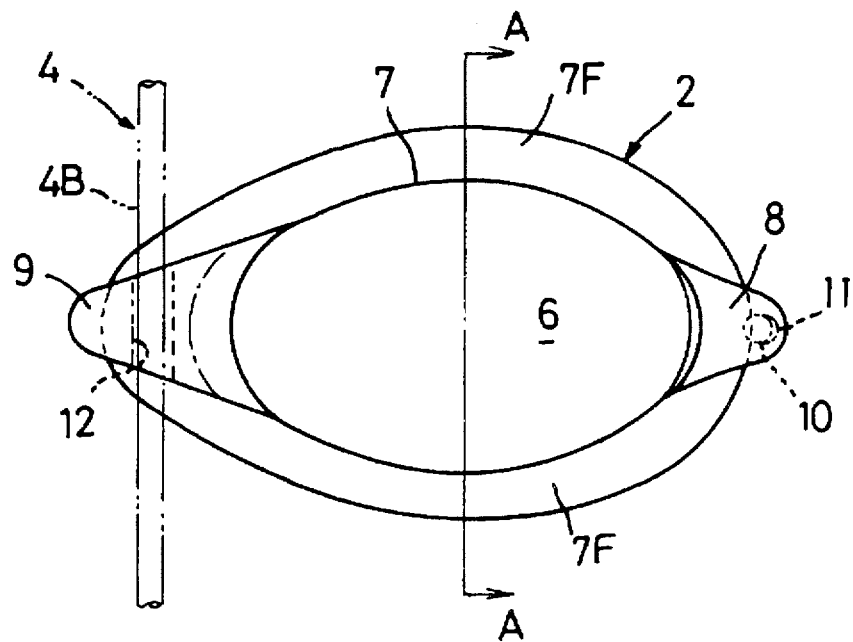
FIG. 2 is an enlarged front view of an eyecup of the embodiment.

FIGS. 1 to 13 illustrate one embodiment of the present invention. Referring to FIG. 1, goggles 1 include a pair of right and left eyecups 2,2, a nasal belt 3, an elastic band 4 and a band buckle 5.

The eyecups 2,2 are formed of a transparent rigid plastic and each include a planar front lens portion 6 and a peripheral wall portion 7 rearwardly extending from the peripheral edge of the lens portion 6. The peripheral wall portion 7 has a rear edge portion 7A having a gently curved surface so as to be well fitted onto wearer's face without the need of a pad. The peripheral wall portion 7 of each eyecup 2 has an inner side portion opposing the corresponding portion of the other eyecup 2, which inner side portion is provided with an inwardly protruding mount portion 8 for mounting the nasal belt 3. An outer end portion of the peripheral wall 7 forms a band connecting portion 9.

Figure 5:
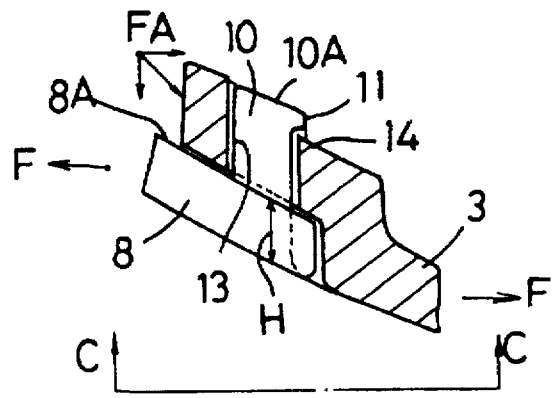
FIG. 5 is an enlarged view of portion B shown in FIG. 3.

The mount portion 8 of each eyecup 2 protrudes diagonally forward beyond the front face of the lens portion 6. The mount portion 8 has a rear face (slanted surface on the wearer's face side) 8A provided with a stick-like projection 10 having a substantially circular section and projecting toward the wearer's face. The projection 10 is acute-angled with respect to the rear face 8A on the peripheral wall side. As shown in FIG. 5, the projection 10 has a rear end face 10A which is inclined with respect to the central axis of the projection 10 so as to be substantially parallel to the rear face 8A of the mount portion 8. The stick-like projection has an engaging protrusion 11 on the inner side of the rear end thereof.

The outer side (the side opposite to the mount portion 8) of the peripheral wall portion 7 of each eyecup 2 extends slantingly rearward to form the band connecting portion 9 which is relatively thick and which defines a band insertion hole 12 extending vertically.

Figure 7:
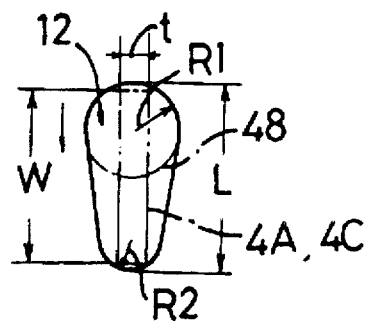
FIG. 7 is a plan view showing the shape of a band insertion hole defined in each eyecup of the embodiment.
Figure 8:
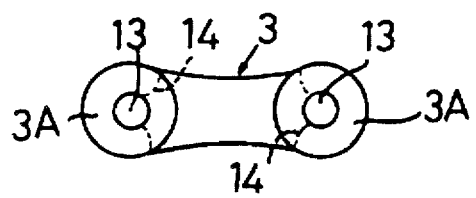
FIG. 8 is a front view of a nasal belt of the embodiment.
Figure 9:
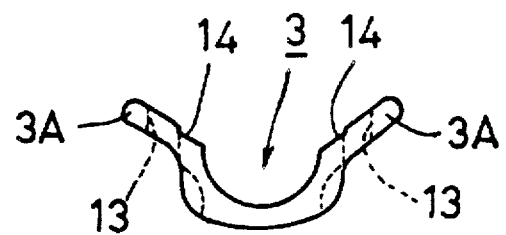
FIG. 9 is a top plan view of FIG. 8.

The band insertion hole 12 is substantially egg-shaped in section having a longer axis (length L) extending in substantially the forward or rearward direction, as shown in FIG. 7. The round rear end portion of the band insertion hole 12 has a radius of curvature R1 larger than the radius of curvature R2 of the round front end portion. The shape and size of the band insertion hole 12 are determined corresponding to the shape and size of the elastic band 4 to be described later.

The nasal belt 3 is curved in plan as shown in FIGS. 1, 3, 5 and 9 and is formed of an elastic material such as a soft or semi-rigid plastic. The nasal belt 3 has longitudinal end portions 3A extending slantingly rearward and respectively having projection engaging holes 13,13 extending therethrough in the forward or rearward direction. Each of the projection engaging holes 13,13 extends diagonal with respect to the front and rear faces of each end portion 3A.

The front face of each end portion 3A is provided with a step H which is recessed relative to the central front face of the nasal belt 3 and sized substantially the same as the thickness of the mount portion 8 measured in the forward or rearward direction (refer to FIG. 5). This step H serves to render the front face of the mount portion 8 of each eyecup substantially flush with the central front face of the nasal belt 3. This feature, when applied to swimming goggles, is advantageous in reducing the resistance of water to the goggles.

Since the projection engaging hole 13 is shaped circular, the stick-like projection 10 having a circular cross section, when fitted into the projection engaging hole 13, allows each eyecup 2 and the nasal belt 3 to pivot therearound relative to each other. The rear face of each end portion 3A of the nasal belt 3 has on the inner end side thereof a cutout 14 for engaging the engaging protrusion 11.

The elastic band 4 is expansible and contractible since it is formed of an elastic material such as rubber. The elastic band 4 comprises a strap-shaped longitudinal central portion 4A having a substantially rectangular cross section, strap-shaped longitudinal end portions 4C having a substantially rectangular cross section, and remaining cord-like intermediate portions 4B having a substantially circular cross section, all of which are integrally molded into the elastic band. The central portion 4A and the end portions 4C have a width W slightly narrower than the longitudinal length L of the band insertion hole 12, so as to pass through the band insertion holes 12 without difficulty (refer to FIG. 7). It should be noted that even if the width W is substantially equal to the length L of the band insertion hole 12, it is possible to insert the elastic band 4 through the band insertion holes 12 with ease by virtue of elastic deformation of the band 4.

The intermediate portions 4B have a radius equal to or slightly smaller than the radius of curvature R1 of the round rear end portion of the band insertion hole 12 of each eyecup 2. Thickness t of the strap-shaped central portion 4A and end portions 4C is equal to or slightly smaller than the value twice as large as the radius of curvature R2 of the round front end portion, which is situated on the lens portion 6 side, of the band insertion hole 12 (refer to FIG. 7). When the elastic band is in position as inserted through the band insertion holes 12, the cord-like intermediate portions 4B are each located as extending through the corresponding band insertion hole 12. Thus, the elastic band 4 is less movable longitudinally of the insertion hole 12 (in the forward or rearward direction of the eyecups 2,2), with the result that the elastic band 4 is unlikely to move back and forth relative to the eyecups 2,2 when the goggles are not worn, ensuring positional stability.

Further, since each cord-like intermediate portion 4B located as extending through the corresponding band insertion hole 12 is substantially circular in cross section, the eyecups 2,2 and the elastic band 4 are pivotable or rotatable relative to each other. This provides an increased degree of fitting freedom of the eyecups 2,2 onto the wearer's face. If the elastic band is twisted, the cord-like intermediate portions 4B absorbs the twisting stress thereby enabling stable fine adjustments. For these reasons, such configuration is highly suitable for goggles designed for competitive swimming which do not employ cushion pads.

The band buckle 5 is formed of a rigid plastic and configured to fasten the both end portions 4C of the elastic band 4 in a superposed manner by allowing the end portions 4C to be inserted therethrough individually. The buckle 5 allows the wearing length of the band 4 to be adjusted depending on the size of the wearer's head while at the same time interconnecting the both ends portions 4C of the elastic band. Thus, the strap-shaped central portion 4A and the both end portions 4C of the elastic band 4 can both be supported by the back of the wearer's head thereby double-supporting the goggles stably and providing improved fit.

Figure 4:
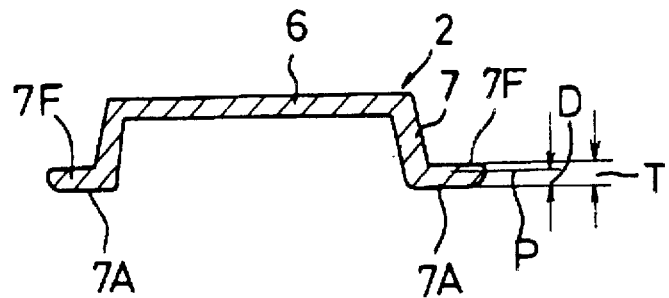
FIG. 4 is a sectional view taken along line A—A of FIG. 2.
Figure 10:
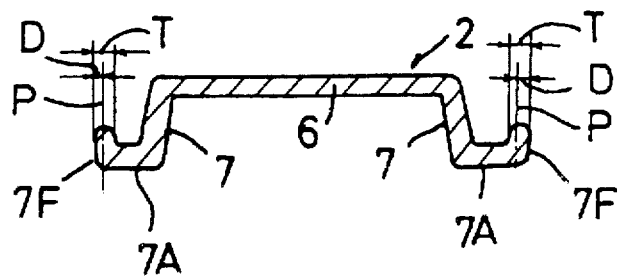
FIG. 10 is a sectional view showing another form of an eyecup of the embodiment.

In molding each eyecup 2, as shown in FIGS. 4 and 10, parting line P is positioned to extend on the line apart from the rear edge face 7A of the peripheral wall portion 7 or from the outer end face of flange portion 7F by a distance D which is greater than the half of the thickness T of the peripheral wall portion 7 or flange portion 7F. Consequently, even if the rear edge face 7A of the peripheral wall portion comes into direct contact with the wearer's face, it contacts the wearer's face softly or gently and does not cause any pain or any feeling of physical disorder.

Figure 6:
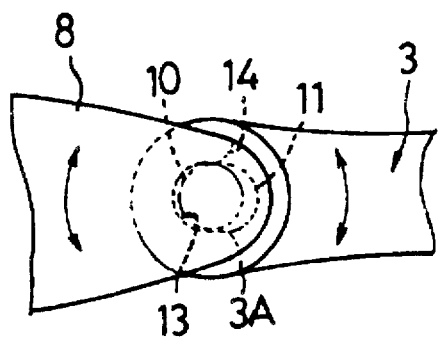
FIG. 6 is a front view of portion B as viewed from line C—C of FIG. 5.

According to the foregoing embodiment, the right and left eyecups 2,2 each pivot about the corresponding stick-like projection 10 relative to the nasal belt 3 as indicated by the arrows in FIG. 6 in wearing the goggles 1. This permits flexible vertical movements of the eyecups, so that the rear edge faces 7A of the eyecups fit the wearer's face. Further, each eyecup 2 can pivot back and forth as indicated by arrows X and Y in FIG. 3 about the corresponding intermediate portion 4B of the elastic band 4 thereby facilitating positional adjustments thereof.

Figure 3:
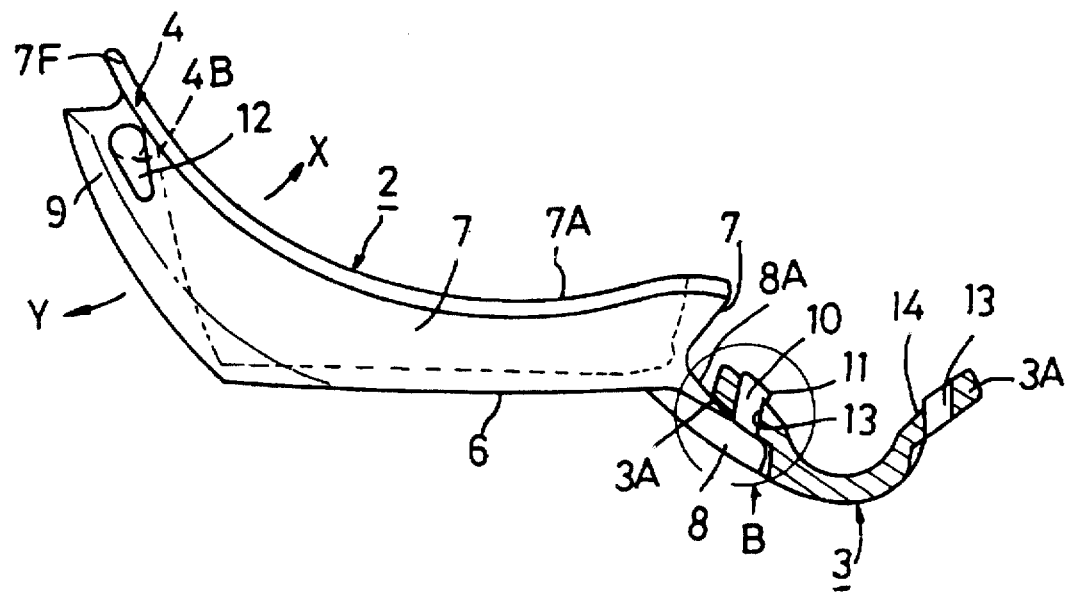
FIG. 3 is a plan view of FIG. 2.

When the goggles 1 are being worn by the wearer, tension F of the elastic band 4 works on the eyecups 2,2 and the nasal belt 3 in the directions indicated by arrows in FIG. 5, so that a force in the direction indicated by arrow FA in FIG. 3 is exerted on each end portion 3A of the nasal belt 3. Thus, the outer half of the peripheral wall of the projection engaging hole 13 is pressed into the angled space between the mount portion 8 and the stick-like projection 10 of each eyecup 2, while the engaging protrusion 11 of the stick-like projection 10 securely engages the cutout portion 14 of the projection engaging portion 13 of the nasal belt 3. Thus, during use of the goggles 1 the stick-like projection 10 will never come off from the engaging hole 13 and, hence, the eyecups 2,2 and the nasal belt 3 will never be separated from each other.

Since the elastic band 4 is vertically inserted through the band insertion holes 12 of the eyecups 2,2, the eyecups 2,2 are unlikely to be twisted, resulting in favorable fit properties. Further, since the strap-shaped portions 4A and 4c of the elastic band 4 are adapted to be located on the back of the wearer's head, the elastic band 4, hence, the eyecups 2,2 can be stably supported. Moreover, the intermediate portions 4B having a substantially circular cross section are located on the side portions of the wearer's face, the goggles 1, if applied to swimming goggles, will be subjected to a decreased resistance of water and hence are best suited for competitive swimming.

Figure 11:
FIG. 11 is a perspective view showing another form of an engaging protrusion of a stick-like projection of the eyecup.
Figure 12:
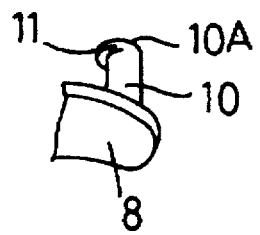
FIG. 12 is a perspective view showing yet another form of the engaging protrusion.
Figure 13:
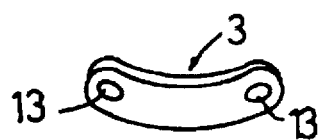
FIG. 13 is a perspective view showing another form of the nasal belt of the embodiment.
Figure 14:
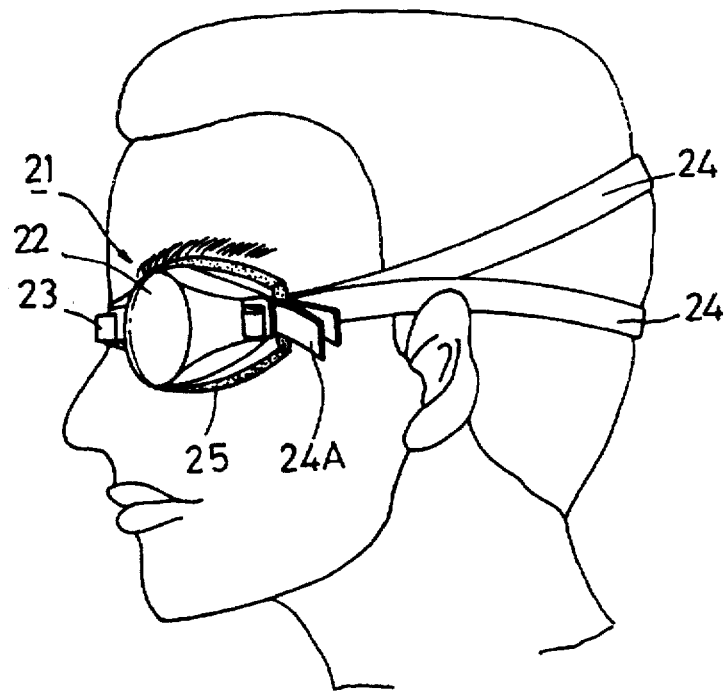
FIG. 14 is a side view of conventional goggles as fitted onto a head.
Figure 15:
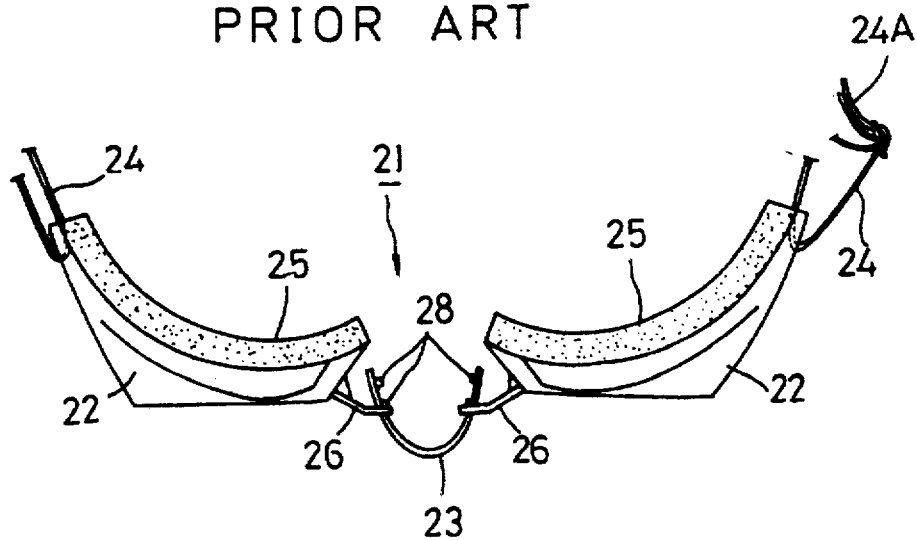
FIG. 15 is an enlarged plan view of the conventional goggles.
Figure 16:
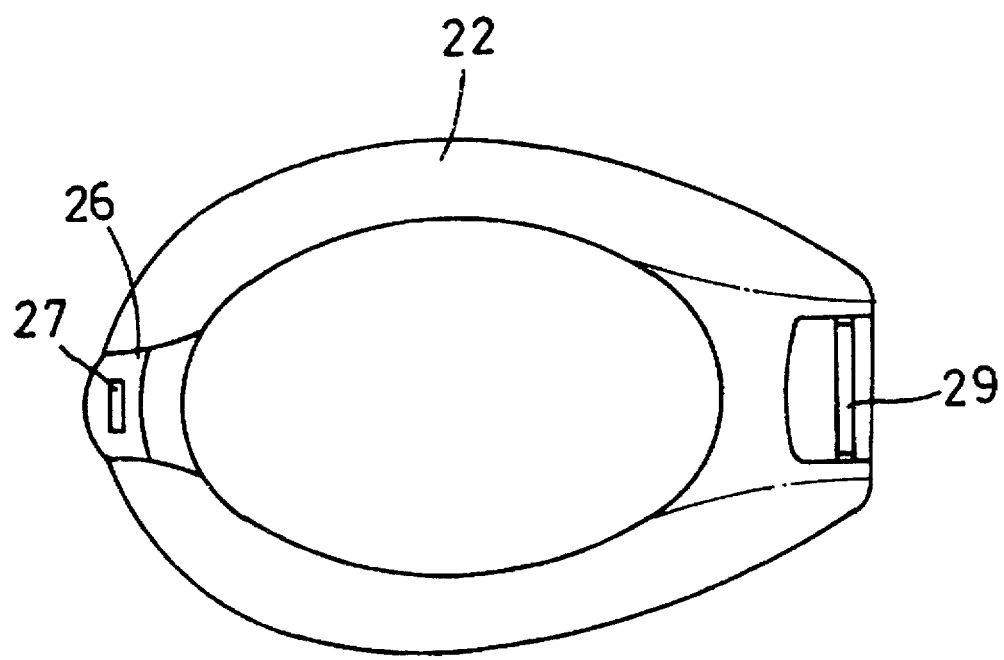
FIG. 16 is a front view showing an eyecup of the conventional goggles.

In the foregoing embodiment the engaging protrusion 11 of the stick-like projection 11 may be configured to extend along the entire peripheral edge of the end portion of the projection 10 as shown in FIG. 11, or otherwise may protrude toward the peripheral wall 7 side of the adjacent eyecup 2 as shown in FIG. 12. The nasal belt 3 may be in the form of a strap as shown in FIG. 13.

It should be noted that the foregoing embodiment is not limitative of the present invention and may be modified in design within the scope of the present invention. For example, the stick-like projection 10 may be formed on the front face of each mount portion 8; the nasal belt 3 may be provided with a stick-like projection, while the mount portion 8 of each eyecup 2 may be formed with a projection engaging hole; each eyecup 2 may be bonded with a cushion pad on the rear edge face 7A of the peripheral wall portion 7; the band insertion hole of each eyecup may be configured substantially circular, egg-shaped, elliptic, substantially oval or the like; and the elastic band may be shaped substantially circular in section throughout the entire length thereof.

Further, the present invention is applicable to any goggles having a nasal belt and mount portions of conventional forms.

As has been described, the present invention is characterized by the band insertion hole extending vertically through the outer end portion of each eyecup. This feature allows the eyecups to be adaptable to forward and rearward movements and vertically movements, prevents the elastic band from twisting the eyecups forward and rearward, and provides improved positional stability and an increased degree of fitting freedom.

The present invention is yet characterized in that the band insertion hole has an elongate circular configuration with its longitudinal front end portion on the lens portion side having a radius of curvature smaller than that of the opposite longitudinal rear end portion on the outer end side of each eyecup. This feature enables easy insertion of the elastic band through the band insertion holes, provides the eyecups with adaptability to movements, and facilitates fine positional adjustments of the goggles.

The present invention is further characterized by the elastic band comprising portions having a substantially circular cross sectional configuration and portions having a substantially rectangular cross sectional configuration. This feature contributes to a weight reduction of goggles, allows the portions having a substantially circular cross sectional configuration to absorb the twisting stress produced when the elastic band is twisted thereby ensuring improved positional stability and easy fine adjustments.

The present invention is still characterized in that the portions having a substantially circular cross sectional configuration of the elastic band have a radius equal to or slightly smaller than the larger radius of curvature of the band insertion hole, while the portions having a substantially rectangular cross sectional configuration have a width equal to or slightly smaller than the longitudinal size of the band insertion hole. This feature enables easy insertion of the elastic band through the band insertion holes, and can hold the elastic band in position.

The present invention is yet still characterized in that the portions having a substantially cross sectional configuration of the elastic band are adapted to be located as extending through the corresponding band insertion holes, while the portion having a substantially rectangular cross sectional configuration of the elastic band are adapted to be located on the back of the wearer's head. This feature allows the eyecups to be adaptable to forward and rearward movements, facilitates fine positional adjustments of the eyecups, enables the goggles to be subjected to decreased resistance of water when applied to swimming goggles for competitive swimming, and provides the goggles with improved positional stability by virtue of double support at the back of the wearer's head.

The present invention is further characterized by the eyecups each having a peripheral wall having a rear edge face adapted to come into direct contact with the wearer's face. This feature eliminates the need of cushion pads thereby realizing reduction in weight and cost. Such goggles are best suited for competitive swimming.

What is claimed is:

1. Goggles comprising right and left eyecups, each eyecup having an inner end portion and an outer end portion and a lens portion, each of said eyecups supporting said lens portion in a generally predetermined direction, a nasal belt interconnecting respective opposing inner end portions of the eyecups, and an elastic band connecting to respective outer end portions of the eyecups, each of the outer end portions of the eyecups defining a band insertion hole extending therethrough, each of said band insertion holes having a longitudinal axis perpendicular to a line extending through said outer end and inner end portions, wherein said band insertion hole of each eyecup is oriented such that a longitudinal axis of a portion of said elastic band extending therethrough is oriented substantially in the predetermined direction.

2. Goggles as set forth in claim 1, wherein the band insertion hole is formed into an elongate circular configuration having a longitudinal end portion with a smaller radius of curvature on a side closer to said lens portion of each eyecup than a larger radius of curvature of an opposite longitudinal end portion on the side closer to the outer end portion of the eyecup.

3. Goggles as set forth in claim 1, wherein the elastic band comprises portions having a substantially circular cross sectional configuration and portions having a substantially rectangular cross sectional configuration.

4. Goggles as set forth in claim 2, wherein the elastic band comprises portions having a substantially circular cross sectional configuration and portions having a substantially rectangular cross sectional configuration, said elastic band portions having a substantially circular cross sectional configuration of the elastic band have a radius equal to or slightly smaller than said larger radius of curvature of the band insertion hole, while the portions having a substantially rectangular cross sectional configuration of the elastic band have a width equal to or slightly smaller than a longitudinal size of the band insertion hole.

5. Goggles as set forth in claim 3, wherein the portions having a substantially circular cross sectional configuration of the elastic band are adapted to be located as extending through the band insertion holes of the eyecups, while the portions having a substantially rectangular cross sectional configuration of the elastic band are adapted to be located on a back of a wearer's head.

6. Goggles as set forth in claim 1, wherein the eyecups each have a peripheral wall having a rear edge face adapted to come into direct contact with a wearer's face.

* * * * *

UNITED STATES PATENT AND TRADEMARK OFFICE
CERTIFICATE OF CORRECTION

PATENT NO.   : 5,711,036
DATED        : January 27, 1998
INVENTOR(S)  : Tadashi KITA, et al.

It is certified that error appears in the above-identified patent and that said Letters Patent is hereby corrected as shown below:

On the title page, item[30] should be:

--[30]    Foreign Application Priority Data

Dec. 25, 1995   [JP]   Japan ......... 7-337519   --

Signed and Sealed this

Seventh Day of April, 1998

Attest:

BRUCE LEHMAN

*Attesting Officer*      *Commissioner of Patents and Trademarks*